United States Patent [19]

Newman

[11] Patent Number: 5,237,069

[45] Date of Patent: Aug. 17, 1993

[54] HYDRIDOTRIS(PYRAZOLYL)BORATE METAL COMPLEXES AND POLYMERIZATION PROCESS

[75] Inventor: Thomas H. Newman, Midland, Mich.

[73] Assignee: The Dow Chemical Company, Midland, Mich.

[21] Appl. No.: 603,350

[22] Filed: Oct. 26, 1990

[51] Int. Cl.$^5$ .......................................... C07D 231/10
[52] U.S. Cl. ..................................... 548/110
[58] Field of Search ........................................ 548/110

[56] References Cited

U.S. PATENT DOCUMENTS 4,808,680  2/1989  Schmidt et al. .
4,870,042  9/1989  Kohara et al. ...................... 502/114

OTHER PUBLICATIONS

Chemical Abstracts, vol. 111, Aug. 21–Sep. 4, 1989, p. 824, 69728w, Kresinski et al.
Chemical Abstracts, vol. 98, No. 16, Apr. 18, 1983, p. 661, 136560p, Reger et al.
Chemical Abstracts, vol. 85, Oct. 4–18, 1976, p. 638, 103138k, Kouba et al.
Chemical Abstracts, vol. 111, Nov. 13–20, 1989, p. 827, 186250v, Hughes et al.
Greaves, W. W.; Angelici R. J.; Inorg. Chem., vol. 20, 2983–2988 (1981), Thiocarbonyl Complexes of cyclopentadienyltungsten and [Hydrotis(1-pyrazolyl)borato]tungsten. Reactions at the CS Ligand Leading to Mercaptocarbyne and Isocyanide Complexes.
Trofimenko, S.; J. Am. Chem. Soc., 91:3, 588–595 (1968) Transition Metal Polypyrazolylborates Containing Other Ligands.
Trofimenko, S.; J. Am. Chem. Soc., 89:13, 3170–3177 (1967) Boron-Pyrazole Chemistry, II Poly(-1-pyrazolyl)borates.

*Primary Examiner*—Mary C. Lee
*Assistant Examiner*—Joseph K. McKane

[57] ABSTRACT

Hydridotris(pyrazolyl)borate complexes of Group 4 metals of the Periodic Table of the Elements and their use in coordination polymerization processes are disclosed.

5 Claims, No Drawings

HYDRIDOTRIS(PYRAZOLYL)BORATE METAL COMPLEXES AND POLYMERIZATION PROCESS

The present invention pertains to novel hydridotris(-pyrazolyl)borate complexes of Group 4 metals of the Periodic table of the Elements and to the use of such complexes as coordination polymerization catalysts. In addition the invention relates to a novel process for polymerizing vinyl aromatic monomers, particularly styrene, to produce syndiotactic polymers.

In U.S. Pat. No. 4,808,680 a process for preparing syndiotactic polystyrene utilizing cyclopentadienyl zirconium trialkoxides, trihalides, etc. and polymethylaluminoxane was disclosed. Complexes having similar or increased catalytic effectiveness but lacking in cyclopentadienyl functionality have been sought without success. The present inventor has now discovered such complexes.

According to the present invention there is now provided a novel complex corresponding to the formula:

$$HY \cdot M \cdot X'_n \cdot X_3 \text{ (I) or } [HY \cdot M \cdot X'_n \cdot X_2]^+ A^- \quad (II)$$

wherein:
HY is a hydridotris(pyrazolyl)borate ion;
M is a metal of Group 4 of the Periodic Table of the Elements;
X each occurrence is an inert anionic ligand;
X' is an inert, neutral donor ligand;
n is 0 or 1: and
$A^-$ is a noncoordinating, compatible anion of a Bronsted acid salt.

In a further embodiment of the invention there is provided a catalyst for coordination polymerizations comprising the aforementioned complexes (I) or (II). When complex (I) is utilized it is beneficial to provide a cocatalyst comprising an aluminum compound containing one or more Al—O, Al—N or Al—P bonds and optionally an aluminum trialkyl compound containing from 1 to 6 carbons in each alkyl group.

Illustrative but nonlimiting examples of X include R, halo, $NR_2$, $PR_2$, OR, SR, and $BR_2$, wherein R is independently each occurrence an aliphatic, cycloaliphatic or aromatic hydrocarbyl group having from 1 to 12 carbon atoms, a silyl or germyl group of from 1 to 12 silicon or germanium atoms, or a substituted derivative thereof.

Illustrative but nonlimiting examples of X' include ROR, RSR, $NR_3$, $PR_3$, wherein R is as previously defined, $C_{2-20}$ olefin or diolefins, etc. Such donor ligands are able to form shared electron bonds but not a formal covalent bond. Preferably n is 0.

All reference to the Periodic Table of the Elements herein shall refer to the Periodic Table of the Elements, published and copyrighted by CRC Press, Inc., 1989. Also, any reference to a Group or Series shall be to the Group or Series as reflected in this Periodic Table of the Elements, utilizing the IUPAC system for numbering groups.

Also as used herein, the term "substituted" when used with reference to R means such groups bearing one or more covalently bonded substituents that do not interfere with the essential nature of the principal group and are inert. The term "inert" means noninterfering with the complex's preparation or with the use of the resulting metal complex as a polymerization catalyst. Examples of substituted R groups include: aralkyl, alkaryl, haloalkyl, silylalkyl, haloalkyl, haloaryl, haloalkaryl, halosilyl, haloalkarylsilyl, alkoxyalkyl, and so forth.

By the term "aromatic" is included both substituted and unsubstituted aryl groups. Preferably X in the complexes of formula (I) is in each occurrence OR, and R is selected from the group consisting of phenyl, and $C_{1-6}$ alkyl or cycloalkyl groups. Most preferably X each occurrence is $C_{1-6}$ alkoxide. Preferably X in the complexes of formula (II) is in each occurrence R, and R is selected from the group consisting of phenyl, and $C_{1-6}$ alkyl or cycloalkyl groups. Most preferably X each occurrence is $C_{1-6}$ alkyl.

Hydridotris(pyrazolyl)borate complexes of metals of Group 4 of the Periodic Table of the Elements are prepared by combining an alkali metal hydridotris(-pyrazolyl)borate compound with a halogenated Group 4 metal compound corresponding to the desired complex or subsequently convertible into the desired complex. Thus suitable Group 4 metal compounds correspond to the formula:

$$X''M \cdot X' \cdot X_3,$$

wherein:
X" is halo, especially chloro, and
M, X' and X are as previously defined.

With respect to the hydridotris(pyrazolyl)borate derivatives, suitable pyrazolyl groups include pyrazolyl itself, ie.

as well as inertly substituted monovalent pyrazol derivatives. Examples include $C_{1-6}$ alkyl pyrazolyl derivatives such as 3,5-dimethylpyrazolyl, trimethylpyrazolyl, etc. A preferred alkali metal hydridotris(pyrazolyl)borate compound is potassium hydridotris(pyrazolyl)borate. The procedure for preparing the complexes of the invention is analogous to that described in Inorg. Chem., 20, 2983, (1981), J. Amer. Chem. Soc. 89, 3170 (1967) and J. Amer. Chem. Soc. 91, 588 (1969).

The complex of formula (I) is rendered catalytically effective by combining the same with an aluminum compound containing one or more Al—O, Al—N or Al—P bonds, as previously mentioned. Preferred aluminum compounds are the well known alkylaluminoxanes, also known as polyalkylaluminoxanes. A highly preferred aluminum compound is methylaluminoxane (MAO). Preferably M is titanium or zirconium.

Effective coordination catalysts are formed from the complexes of formula (I) in the presence of an aliphatic, cycloaliphatic or aromatic solvent or a combination of such solvents. The components are employed in quantities which provide an atomic ratio of MAO:M from 10:1 to 50,000:1, more suitably from 50:1 to 10,000:1, and most suitably from 100:1 to 1000:1.

Alkylaluminoxanes may be prepared according to any known technique. One such technique includes the reaction of a trialkylaluminum, such as trimethylaluminum, and a hydrated metal salt as disclosed by Kaminsky in U.S. Pat. No. 4,544,762, the teachings of which are herein incorporated in their entirety by reference thereto. A preferred technique is the use of a regeneratable aqueous imbiber as disclosed in U.S. Ser.

No. 405,118 filed Sep. 7, 1989. For purposes of calculating the molar ratio of MAO:titanium in the catalysts of the present invention, the polymethylaluminoxane is assigned a repeating unit structure corresponding to the formula: (Al(CH$_3$)O).

The hydridotris(pyrazol)borate metal complex and aluminum compound containing one or more Al—O, Al—N, or Al—P bonds and optional aluminum trialkyl compound are combined in a suitable diluent. In the preparation of the catalyst composition, the metal complex is preferably added in an inert diluent to the various aluminum compounds. The catalyst components may be suitably mixed in an inert atmosphere such as nitrogen, argon, xenon, or combinations thereof. The components are mixed at any suitable temperature, preferably from 0° C. to 100° C., more suitably from 25° C to 50° C. The metal complex (I) may also be combined with the aluminum containing compounds in the presence of the monomer to be polymerized if desired.

A further beneficial effect is also observed both in catalytic efficiency and in rate of catalyst formation if an aluminum trialkyl compound is also incorporated into the catalyst. Examples of suitable trialkyl aluminum compounds include trimethyl aluminum, triethyl aluminum, triisopropyl aluminum, triisobutyl aluminum, etc. A preferred trialkyl aluminum compound is triisobutyl aluminum.

The aluminum trialkyl compound may be utilized in an amount to provide an atomic ratio of aluminum trialkyl:M of 0:1 to 50,000:1, more suitably from 50:1 to 10,000:1, and most suitably from 100:1 to 1000:1.

The complexes of formula (II) are catalytically effective without the need for a cocatalyst or for an aluminum trialkyl compound. They are prepared by combining at least two components as hereinafter disclosed. The first component is a derivative of a Group 4 metal containing at least one substituent which will combine with the cation of a second component (described hereinafter) or alternatively which is subject to oxidative activation as hereinafter described. The first component additionally must be capable of forming a cation formally having a coordination number that is one less than its valence.

The second component is a salt of a Bronsted acid and a noncoordinating compatible anion or alternatively a salt of an oxidizing cation and a noncoordinating, compatible anion. As used herein, the recitation "noncoordinating, compatible anion" means an anion which either does not coordinate with the first component or a derivative thereof, or which is only weakly coordinated to said component thereby remaining sufficiently labile to be displaced by the monomer to be polymerized. The recitation "noncoordinating, compatible anion" specifically refers to an anion which when functioning as a charge balancing anion does not transfer an anionic substituent or fragment thereof to the cationic portion of the catalyst. Compatible anions are also anions which are not degraded to neutrality under the reaction conditions of the present invention.

More preferably such metal derivative compounds are those having organyl substituents that are either devoid of reactive hydrogens or wherein potentially reactive hydrogens are protected by bulky protecting groups. Illustrative, but not limiting examples of suitable metal derivative compounds include: [hydridotris(-pyrazolyl)borate]tribenzylzirconium, [hydridotris(-pyrazolyl)borate]tribenzyltitanium, [hydridotris(-pyrazolyl)borate]trimethyltitanium, [hydridotris(-pyrazolyl)borate]trimethylzirconium, [hydridotris(-pyrazolyl)borate]trineopentyltitanium, [hydridotris(-pyrazolyl)borate]triphenylzirconium, [hydridotris(-pyrazolyl)borate]trineopentylzirconium, [hydridotris(-pyrazolyl)borate]di(m-tolyl)titanium, [hydridotris(-pyrazolyl)borate]di(p-tolyl)zirconium, [hydridotris(-pyrazolyl)borate]trimethyltitanium hydride, [hydridotris(pyrazolyl)borate]tri(diphenylmethyl)zirconium, hydridotris(pyrazolyl)borate]diphenylmethylzirconium, [hydridotris(pyrazolylborate)]dimethyl-(isopropoxy)-titanium, [hydridotris(pyrazolyl]borate)-di(isopropoxy)-titanium, [hydridotris(pyrazolylborate)]dibenzyl(phenoxy)zirconium, [hydridotris(-pyrazolyl)borate]dibenzyl(isopropoxy)zirconium, [hydridotris(pyrazolyl)borate]dimethyltitanium chloride, [hydridotris(pyrazolyl)borate]methylhafnium chloride, [hydridotris(3,5-dimethylpyrazolyl)borate]tribenzylzirconium, [hydridotris(trimethylpyrazolyl)borate]tribenzyltitanium, [hydridotris(3,5-diethylpyrazolyl)borate]-trimethyltitanium, [hydridotris(trimethylpyrazolyl)-borate]trimethylzirconium, [hydridotris(3,5-dimethylpyrazolyl)borate]trineopentyltitanium, [hydridotris(3,5 dimethylpyrazolyl)borate]triphenylzirconium, [hydridotris(trimethylpyrazolyl)boratetrineopentylzirconium, [hydridotris(trimethylpyrazolyl)borate]dimethyltitanium chloride, [hydridotris(3,5-dimethylpyrazolyl)borate]methylhafnium chloride, and the like.

Other compounds which are useful in the catalyst compositions of formula (II) will, of course, be apparent to those skilled in the art. Preferred are titanium or zirconium compounds.

Compounds useful as a second component in the preparation of the complexes of formula (II) may, in one embodiment, comprise a cation, which is a Bronsted acid capable of donating a proton, and a compatible, noncoordinating anion. In another embodiment such compounds comprise an oxidizing cation and a compatible, noncoordinating anion. Preferred anions are those containing a single coordination complex comprising a charge-bearing metal or metalloid core which anion is relatively large (bulky), capable of stabilizing the active Group 4 cation formed when the two components are combined, and which will be sufficiently labile to be displaced by the polymerizable monomer.

The recitation "metalloid", as used herein, includes non-metals such as boron, phosphorus and the like which exhibit semi-metallic characteristics. Suitable metals, include, but are not limited to, aluminum, gold, platinum and the like. Suitable metalloids include, but are not limited to, boron, phosphorus, silicon and the like. Compounds containing anions which comprise coordination complexes containing a single metal or metalloid atom are, of course, well known. In light of this, salts containing anions comprising a coordination complex containing a single boron atom are preferred.

Preferably, second components useful in the preparation of the complexes of formula (II) may be represented by the following general formulas:

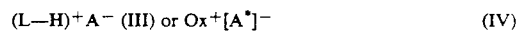

(L—H)$^+$A$^-$ (III) or Ox$^+$[A$^*$]$^-$ (IV)

wherein:
L is a neutral Lewis base;
(L—H)$^+$ is a Bronsted acid:
A$^-$ is a compatible, noncoordinating anion;
Ox$^+$ is an organic or metallic oxidizing cation: and
[A$^*$]$^-$ is a compatible, noncoordinating, inert, anion.

By the term "inert" as employed above is meant that A* of formula (IV) comprises an anion which is a single coordination complex comprising a plurality of lipophilic radicals covalently coordinated to and shielding a central formally charge-bearing metal or metalloid atom, which anion is bulky and stable under the oxidation and subsequent polymerization conditions, and which anion is compatible with and noncoordinating towards the resulting polymerization catalyst. The anion is employed only to provide charge balance without interfering with the oxidizing ability of $Ox^+$.

Preferably $A^-$ corresponds to the formula:

$$[M'Q_{n'}]^-$$

wherein:
M' is a metal or metalloid selected from Groups 5–15 of the Periodic Table of the Elements;
Q independently each occurrence is selected from the Group consisting of hydride, dialkylamido, halide, alkoxide, aryloxide, hydrocarbyl, and substituted-hydrocarbyl radicals of up to 20 carbons with the proviso that in not more than one occurrence is Q halide;
n' is an integer from 2 to 8; and
n—m=1:

Second components of formula (111) comprising boron are particularly useful in the preparation of catalysts of the invention and may be represented by the following general formula:

$$[L-H]^{+}[BQ_4]^{-}$$

wherein:
L is a neutral Lewis base;
$[L-H]^+$ is a Bronsted acid:
B is boron in a valence state of 3; and
Q is as previously defined.

Illustrative, but not limiting, examples of boron compounds which may be used as a second component of formula (III) are trialkyl-substituted ammonium salts such as triethylammonium tetraphenylborate, tripropylammonium tetraphenylborate, tri(n-butyl)ammonium tetraphenylborate, trimethylammonium tetra(p-tolylborate), tributylammonium tetrakis-pentafluorophenylborate, tripropylammonium tetrakis-2,4-dimethylphenylborate, tributylammonium tetrakis-3,5-dimethylphenylborate, triethylammonium tetrakis-(3,5-di-trifluoromethylphenyl)borate and the like. Also suitable are N,N-dialkyl anilinium salts such as N,N-dimethylanilinium tetraphenylborate, N,N-diethylanilinium tetraphenylborate, N,N-2,4,6-pentamethylanilinium tetraphenylborate and the like: dialkyl ammonium salts such as di-(isopropyl)ammonium tetrakis-pentafluorophenylborate, dicyclohexylammonium tetraphenylborate and the like; and triaryl phosphonium salts such as triphenylphosphonium tetraphenylborate, tri(methylphenyl)phosphonium tetrakis-pentafluorophenylborate, tri(dimethylphenyl)phosphonium tetraphenylborate and the like.

Similar lists of suitable compounds containing other metals and metalloids which are useful as constituents of the second components of formula (III) could be made, but such lists are not deemed necessary to a complete disclosure. In this regard, it should be noted that the foregoing lists is not intended to be exhaustive and other boron compounds that would be useful as well as useful components containing other metals or metalloids would be readily apparent from the foregoing general formula and examples to those skilled in the art.

Anions comprising boron which are particularly useful as $[A^*]^-$ may be represented by the following general formula:

$$[BX_1X_2X_3X_4]^-$$

wherein:
B is boron in a valence state of 3;
$X_1$ to $X_4$ are the same or different nonreactive, organyl or silyl radicals containing from 6 to 20 carbon or silicon atoms. In addition two or more of $X_1$ to $X_4$ may be linked to each other through a stable bridging group. Preferably $X_1$ to $X_4$ lack reactive hydrogen moieties. That is, the radicals are either devoid of hydrogen, contain only hydrogen in nonactivated positions or contain sufficient steric hindrance to protect potentially active hydrogen sites. Examples of suitable radicals for $X_1$ to $X_4$ are perfluorinated hydrocarbyl radicals containing from 1 to 20 carbon atoms, 3,4,5-trifluorophenyl, 3,4-di(trifluoromethyl)phenyl, etc.

A most highly preferred compatible, noncoordinating, inert, second component anion corresponding to formula (IV) is tetra(pentafluorophenyl)borate.

Suitable oxidizing cations include organic and inorganic cations having sufficient electronegativity to oxidize the metal derivatives. Organic oxidizing cations for use in the compounds corresponding to formula (IV) include ferrocenium ions, indenium ions and cationic derivatives of substituted ferrocene, indene, and the like molecules. Suitable metallic oxidizing cations include $Ag^{+1}$, $Pd^{+2}$, $Pt^{+2}$, $Hg^{+2}$, $Hg_2^{+2}$, $Au^{30}$ and $Cu^+$. Highly preferred oxidizing cations have an oxidation potential of at least +0.20 volt and preferably at least +0.25 volt. Most highly preferred oxidizing cations are ferrocenium and $Ag^{+1}$ cations.

Without wishing to be bound by any particular theory of operation it is believed that the oxidizing cation causes the molecular oxidation of the metal derivative, and in the process becomes a neutral species. The oxidized metal derivative loses a hydrogen or hydrocarbyl radical by a unimolecular elimination reaction. Two or more such radicals form a hydrogen molecule or a neutral organic species. These byproducts are neutral or noninterfering with any subsequent polymerization reaction and may also be removed from the reaction mixture. The preparation technique is analogous to that previously disclosed by R. Jordan, et al., J. Amer. Chem. Soc., 109, 4111–4113 (1987).

Illustrative, but not limiting, examples of oxidizing agents for use in the second components of formula (IV) are ferrocenium tetra(pentafluorophenyl)borate, gold (I) tetrakis 3,4,5-trifluorophenyl borate, silver tetra(pentafluorophenyl)borate, 1,1'-dimethylferrocenium tetrakis 3,5-bistrifluoromethyl-phenyl borate and the like.

In general, the complex of formula (II) can be prepared by combining the two components in a suitable solvent at a temperature within the range from 0° C. to 100° C., preferably 25° C. to 50° C. When utilized as a catalyst the complex can also be formed in situ if the components thereof are added directly to the polymerization process and a suitable solvent or diluent, including condensed monomer, is used in said polymerization process. It is, however, preferred to form the catalyst in a separate step in a suitable solvent prior to adding the same to the polymerization step. The respective components are generally sensitive to both moisture and oxygen and should be handled and transferred in an inert atmosphere such as nitrogen, argon or helium.

Suitable solvents or diluents include, but are not necessarily limited to, straight and branched-chain hydrocarbons such as $C_{6-12}$ alkanes (hexane, heptane, octane and the like); $C_{6-12}$ cyclic and alicyclic hydrocarbons such as cyclohexane, cycloheptane, methylcyclohexane, methylcycloheptane and the like and $C_{6-12}$ aromatic and alkyl-substituted aromatic compounds such as benzene, toluene, xylene, decalin, and the like, and mixtures of the foregoing.

The complexes may be employed as homogeneous catalysts or supported on the surface of a suitable support such as alumina or silica. The catalysts may be employed to polymerize any coordination polymerizable monomer including $C_{2-10}$ α-olefins, $C_{8-12}$ vinylaromatic monomers, etc.

In a preferred aspect of the present invention there is provided a process for preparing syndiotactic polymers of vinyl aromatic monomers which process comprises contacting at least one polymerizable vinyl aromatic monomer under polymerization conditions in the presence of one of the previously disclosed catalysts. As used herein, the term "syndiotactic" refers to such polymers having a stereoregular structure of greater than 50% syndiotactic as determined by 13C nuclear magnetic resonance spectroscopy. Such polymers may be usefully employed in the preparation of articles and objects (eg., via compression molding or other suitable technique) having an extremely high resistance to deformation due to the effects of temperature.

The polymerization is conducted at temperatures of from 25° C. to 100° C., preferably from 30° C. to 80° C., for a time sufficient to produce the desired polymer. Typical reaction times are from several minutes to several hours, preferably from 1 to 10 hours. The optimum time will vary depending upon the temperature, solvent and other reaction conditions employed. The polymerization of vinyl aromatic monomers is preferably conducted under bulk polymerization conditions.

The polymerization can be conducted at subatmospheric pressure as well as superatmospheric pressure, suitably at reduced pressures such that the lowest boiling component or components of the polymerization mixture do not vaporize up to 100 MPa. For the polymerization of α-olefins, especially highly volatile low molecular weight monomers, elevated pressures from 0.2 to 10 MPa are preferred. In the polymerization of vinyl aromatic monomers it is preferable that near atmospheric pressure be employed.

Suitable vinyl aromatic monomers which can be polymerized in the process of the present invention include those represented by the formula:

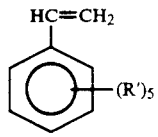

wherein each R' is independently hydrogen, an aliphatic, cycloaliphatic or aromatic hydrocarbon group having from 1 to 10, more suitably from 1 to 6, most suitably from 1 to 4, carbon atoms: or a halogen atom. Preferably such monomers include: styrene, chlorostyrene, n-butyl styrene, etc., with styrene being especially suitable.

The polymerization can be conducted in the presence of an inert diluent. Examples include aliphatic, cycloaliphatic, aromatic and halogenated aromatic hydrocarbons, as well as mixtures thereof. Preferred diluents comprise the $C_{4-20}$ alkanes, especially branched chain alkanes, toluene and mixtures thereof. A particularly desirable diluent for the polymerization is isooctane, or blends thereof such as Isopar-E ®, available from Exxon. Suitable amounts of solvent are employed to provide a monomer concentration from 5% to 100% by weight. During the polymerization, polymer may precipitate from the reaction mixture as it is formed. Preferably vinyl aromatic monomers are polymerized in the absence of a diluent.

As in other similar polymerizations it is highly desirable that the monomers and solvents employed be of sufficiently high purity that catalyst deactivation does not occur. Any suitable technique for monomer and diluent purification such as devolatilization at reduced pressures, contacting with molecular sieves or high surface area alumina, deaeration, etc. may be employed.

Purification of the resulting polymer to remove entrained catalyst may also be desired by the practitioner. Entrained catalyst may generally be identified by residues of ash on pyrolysis of the polymer that are attributable to aluminum and titanium values. A suitable technique for removing such compounds is by solvent extraction, eg. extraction utilizing hot, high boiling chlorinated solvents, followed by filtration.

Having described the invention, the following example is provided as further illustrative and is not to be construed as limiting.

EXAMPLE 1

Under a nitrogen atmosphere, a solution of chlorotitanium triisopropoxide (5.21 g. 0.020 mol) in toluene (100 ml) was added dropwise to a slurry of potassium (hydridotris(pyrazolyl)borate) (5.04 g, 0.020 mol) in 150 ml toluene at 25° C. The resulting mixture was stirred for 16 hours at 25° C. A white precipitate was allowed to settle and the solution was transferred to a second container via a cannula. The volatile components were removed under reduced pressure at 60° C. leaving a white semi-crystalline solid. Identification of the product as [hydridotris(pyrazolyl)borate]titanium triisopropoxide was made on the basis $^1$H and $^{13}$C NMR spectra.

The above complex was combined with methylaluminoxane (MAO) and triisobutyl aluminum (TIBA) to prepare a coordination polymerization catalyst. Accordingly, 10 ml of purified and dried styrene monomer, 75 μL of a 1M triisobutyl aluminum solution in toluene and 37.5 μl of a 2M solution of MAO in toluene were combined in a glass lined, polymerization reactor. Thirty seven and one half μL of a 0.01 M solution of [hydridotris(pyrazolyl)-borate]titanium triisopropoxide in toluene was added to initiate the polymerization. The reactor was held at 70° C. for 4 hours. The reaction was quenched with methanol, and the polymer recovered by filtration and drying. The yield was 0.28 g of a highly crystalline polystyrene having a melting point of 266° C. as determined by differential scanning calorimetry, and a syndiotacticity of 90 percent as determined by $^{13}$C NMR spectroscopy.

EXAMPLE 2

Under a nitrogen atmosphere, a solution of chlorotitanium triisopropoxide (5.21 gm, 0.020 mol) in 50 ml of toluene was added dropwise to a slurry of potassium [hydridotris(3,5-dimethylpyrazolyl)borate] (6.72 gm, 0.020 mol) in 150 ml of toluene at room temperature. The resulting mixture was stirred overnight at room temperature. A fine white precipitate was present in the solution. The solution was filtered to remove the precipitate and the volatiles removed under reduced pressure at 70° C. leaving a white powdery solid. The product was purified by recrystallization from hexane at −10° C. Identification of the product as [hydridotris(3,5-dimethylpyrazolyl)borate]titanium triisopropoxide was made on the basis of the $^1$H NMR spectrum.

The above complex was combined with MAO and TIBA to prepare a coordination polymerization catalyst. The same conditions as Example 1 were utilized. The yield was 0.43 g of syndiotactic polystyrene having a melting point of 266° C. as determined by differential scanning calorimetry.

What is claimed is:

1. A complex corresponding to the formula:

$$HY \cdot M \cdot X'_n \cdot X_3 \text{ or } [HY \cdot M'_n \cdot X_2]^+ \ A^-$$

wherein:
HY is a hydridotris(pyrazolyl)borate ion,
M is a metal of Group 4 of the Periodic Table of the Elements
X each occurrence is an inert anionic ligand selected from the group consisting of R, $NR_2$, $PR_3$, OR, SR and $BR_2$ wherein R is a $C_{1-12}$ hydrocarbyl group;
X' is an inert, neutral donor ligand selected from the group consisting of ROR, RSR, $NR_3$, $PR_3$, wherein R is as previously defined, and $C_{2-20}$ olefins or diolefins;
n is 0 or 1; and
$A^-$ is a noncoordinating, compatible anion of a Bronsted acid salt.

2. A complex according to claim 1 wherein M is titanium.

3. A complex according to claim 1 wherein n is 0.

4. A complex according to claim 1 wherein HY is pyrazolyl or 3,5-dimethyl pyrazolyl.

5. A complex according to claim 1 which is [hydridotris(pyrazolyl)borate]titanium triisopropoxide or [hydridotris(3,5-dimethylpyrazolyl)borate]titanium triisopropoxide.

* * * * *

UNITED STATES PATENT AND TRADEMARK OFFICE
CERTIFICATE OF CORRECTION

PATENT NO. : 5,237,069

DATED : August 17, 1993

INVENTOR(S) : Thomas H. Newman

It is certified that error appears in the above-identified patent and that said Letters Patent is hereby corrected as shown below:

Column 10, line 1, "or $[HY \cdot M'_n \cdot X_2]^+ A^-$" should correctly read: --or $[HY \cdot M \cdot X'_n \cdot X_2]^+ A^-$--.

Signed and Sealed this

Thirtieth Day of May, 1995

Attest:

BRUCE LEHMAN

Attesting Officer

Commissioner of Patents and Trademarks